United States Patent [19]

Parish et al.

[11] Patent Number: 5,598,251
[45] Date of Patent: Jan. 28, 1997

[54] CONCENTRATION SENSING BY VISCOSITY MEASUREMENT

[75] Inventors: George K. Parish, Winchester; William J. Thornhill, Lexington, both of Ky.

[73] Assignee: Lexmark International, Inc., Greenwich, Conn.

[21] Appl. No.: 440,602

[22] Filed: May 15, 1995

[51] Int. Cl.⁶ .................................................. G03G 15/10
[52] U.S. Cl. ............................. 399/30; 73/54.15; 399/237
[58] Field of Search .................................. 355/203, 256; 118/689; 324/661, 663, 665, 677; 73/54.02, 54.15

[56] References Cited

U.S. PATENT DOCUMENTS

| | | | |
|---|---|---|---|
| 3,368,390 | 2/1968 | Norcross | 73/56 |
| 4,343,548 | 8/1982 | Bares et al. | 355/3 DD |
| 5,208,637 | 5/1993 | Landa | 355/256 |

OTHER PUBLICATIONS

Viscosity and Flow Measurement, A Laboratory Handbook of Rheology by J. R. Van Wazer et al, pp. 292–295.

Primary Examiner—Joan H. Pendegrass
Assistant Examiner—Quana M. Grainger
Attorney, Agent, or Firm—John A. Brady

[57] ABSTRACT

In a liquid toner chamber (2) of a copier or printer a top plate (5) is moved upward and allowed to fall. The capacitance between the plates is used to define their separation and the time for the plates to move between predetermined locations is used to define the concentration of the liquid toner. This is accurate and inexpensive, while other measurement systems are not suitable to measure the high concentrations with which this invention functions.

4 Claims, 2 Drawing Sheets

CONCENTRATION SENSING BY VISCOSITY MEASUREMENT

TECHNICAL FIELD

This invention relates to the measurement of the viscosity of liquids and to the continuous sensing of solids concentration in liquids by measurement of viscosity. A particular application is in replenishing liquid toner.

BACKGROUND OF THE INVENTION

To ensure proper toner development and print quality in liquid toner printers and copiers, the liquid toner concentration must be measured and controlled in the liquid toner electrophotographic print process. Several techniques to measure liquid toner concentration or percent solids by weight include optical density, conductivity, permittivity, density and ultrasonic methods. Because high concentration liquid toners have a high light extinction factor, optical techniques are limited to measurement below a few percent solids. Where the operating point is higher, typically approximately eight percent solids, an optical technique is unacceptable. The liquid toner conductivity, permittivity, and density signal to noise ratio is small for changes in toner concentration. High frequency ultrasonic techniques overcome these problems, but are expensive to implement.

U.S. Pat. No. 5,208,637 to Landa discloses optical sensing for replenishment of liquid toner. U.S. Pat. No. 4,343,548 to Bares et al discloses sensing conductivity to replenish toner. This invention uses a transverse flow viscometer, which is a known viscosity measurement technique, to predict the liquid toner concentration. This invention provides a low cost sensor with improved percent solids range and signal to noise ratio.

The liquid toner viscosity is a function of fluid temperature, percent solids, and toner particle size distribution. For a constant particle size distribution, the liquid toner concentration may be predicted by measuring the fluid temperature and viscosity. This invention applies a transverse flow viscometer technique to predict the liquid toner concentration. Transverse flow viscometers and basic theoretical equations employed to develop this invention, are described in the book *Viscosity and Flow Measurement, A Laboratory Handbook of Rheology* by J. R. Van Wazer et al. U.S. Pat. No. 3,368,390 to Norcross is illustrative of known activity to flow viscometers.

DISCLOSURE OF THE INVENTION

A stationary, horizontal bottom plate and a vertically movable, horizontal top plate are suspended in the chamber containing the liquid. The top plate is periodically raised by a motor and then allowed to fall under gravity, allowing the liquid between the plates to be squeezed out laterally. The separation of the plates is measured by the capacity between them, and the time to move a predetermined distance is measured. That time is interpreted as directly indicative to the solids concentration of the liquid.

To provide new representative liquid between the plates, the liquid is drawn in through a check valve in the bottom plate. Upward movement of the top plate creates a pressure differential which opens the check valve to supply liquid between the plates from the area of the liquid chamber under the bottom plate.

A primary application is to replenish liquid toner in an imaging apparatus, such as a printer or copier. The top and bottom plates are located in the chamber of the apparatus holding toner for use.

BRIEF DESCRIPTION OF THE DRAWING

The details of this invention will be described in connection with the accompanying drawing, in which.

BEST MODE FOR CARRYING OUT THE INVENTION

Figure 1:
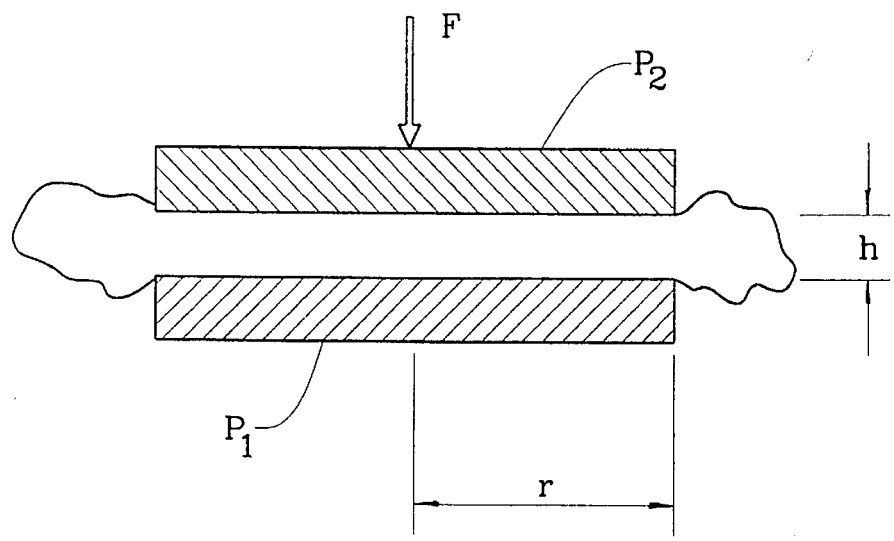
FIG. 1 is illustrative of transverse flow between top and bottom plates.

A transverse flow viscometer consists of two parallel circular plates, $P_1$ and $P_2$ with a radius, r, as shown FIG. 1. The gap, h, is completely filled with fluid and a constant force, F, is applied perpendicular to the plates, As the two plates approach each other, the fluid flows across the surfaces of the plates.

For a Newtonian fluid, the viscosity of the fluid between the plates is $$\frac{-dh}{dt} = \frac{2Fh^3}{3\pi\eta r^4}.$$

Then the relative velocity of the plates following equation $$\eta = \frac{-2Fh^3}{3\pi r^4} \left( \frac{dt}{dh} \right).$$

By separation of parts and straightforward integration between the limits of $h_0$ and h and 0 and t, it can be shown that the plate gap is $$\left( \frac{4Ft}{3\pi\eta r^4} + \frac{1}{h_0^2} \right)^{-1/2};$$

where t is time and $h_0$ is the initial plate gap at time t=0. These equations are found in the foregoing book by Van Wazer et al.

Conversely, by the same result, $$t = \frac{3\pi\eta r^4}{4F} \left( \frac{1}{h^2} - \frac{1}{h_0^2} \right).$$

From the preceding equation, $$t_2 - t_1 = \frac{3\pi\eta r^4}{4F} \left( \frac{1}{h_2^2} - \frac{1}{h_0^2} - \frac{1}{h_1^2} + \frac{1}{h_0^2} \right) = \frac{3\pi\eta r^4}{4F} \left( \frac{1}{h_2^2} - \frac{1}{h_1^2} \right).$$

Since the geometry and the force are constant, the fluid viscosity may be determined by measuring the plate gap and velocity. This may be accomplished by measuring the time it takes the plates to move between two specific gaps, such as $h_1$ and $h_2$. This time measurement will be independent of the initial gap $h_0$.

The gap may be determined by measuring the electrical capacitance between the plates. For parallel circular plates the capacitance $$C = \frac{\pi r^2 k \epsilon_0}{h}$$

where k is the dielectric constant for the fluid and $\epsilon_0$ is the permittivity constant. The time for the plates to move from $h_1$ to $h_2$ can be expressed by the following equation, $$\Delta t = \frac{3\eta}{4\pi F k^2 \epsilon_0^2} \left( C\frac{2}{1} - C\frac{2}{2} \right).$$

This measurement will be independent of the radius of the plates.

Figure 2:
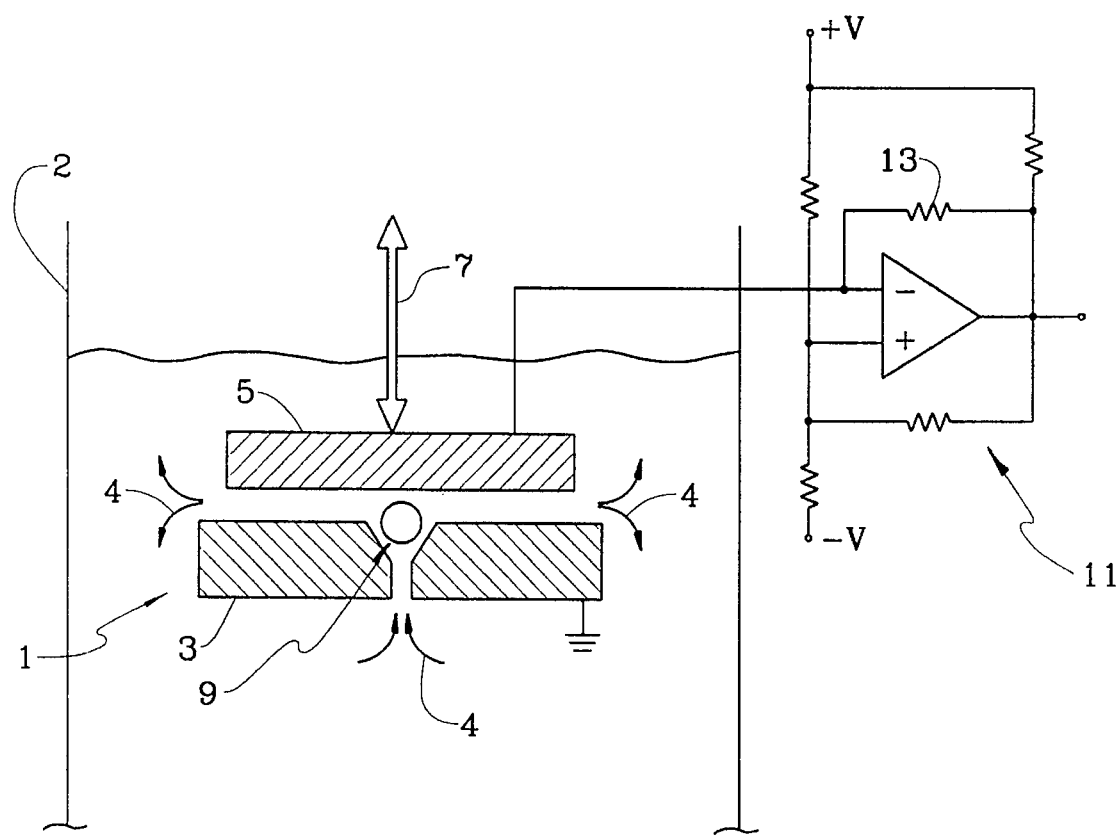
FIG. 2 illustrates the viscosity sensor of this invention.

The preferred liquid toner viscosity sensor is shown in FIG. 2. A transverse flow viscometer 1 is located in a tank or chamber 2 holding liquid toner. The bottom plate 3 of the sensor is stationary and at ground potential. The upper plate is lifted by a cam (not shown) on the agitator motor shaft (shown illustratively as vertical arrow 7) and then allowed to fall due to gravitational force. Arrows show liquid flow. The viscometer cycle rate may be the same as that of an agitator motor (not shown) for tank 2, approximately one hertz, since that motor may be used to raise top plate 5. The maximum gap, $h_0$, is less than a millimeter, Since gravity is fairly constant, the only error in the driving force will be the mass of the upper plate, The mass can be controlled inexpensively. Since the viscometer cycle rate, initial gap and radius are not critical, the sensor is fairly inexpensive.

The invention also features a check valve 9 in the center of the bottom plate 3. When the upper plate 5 that raises, check valve 9 opens and fresh fluid flows into the viscometer. This ensures the sensor will always have representative liquid toner. The plate capacitance measurement technique includes a simple RC oscillator 11 . The frequency of oscillator 11 will be proportional to the resistance of feedback resistor 13 and the capacitance across plates 3 and 5. The measurement error is reduced since the oscillator frequency is independent of power supply variations. A feature of oscillator 11 is that it allows the potential of the upper plate 5 to swing above and below ground, which prevents toner from contaminating the plate surfaces.

Figure 3:
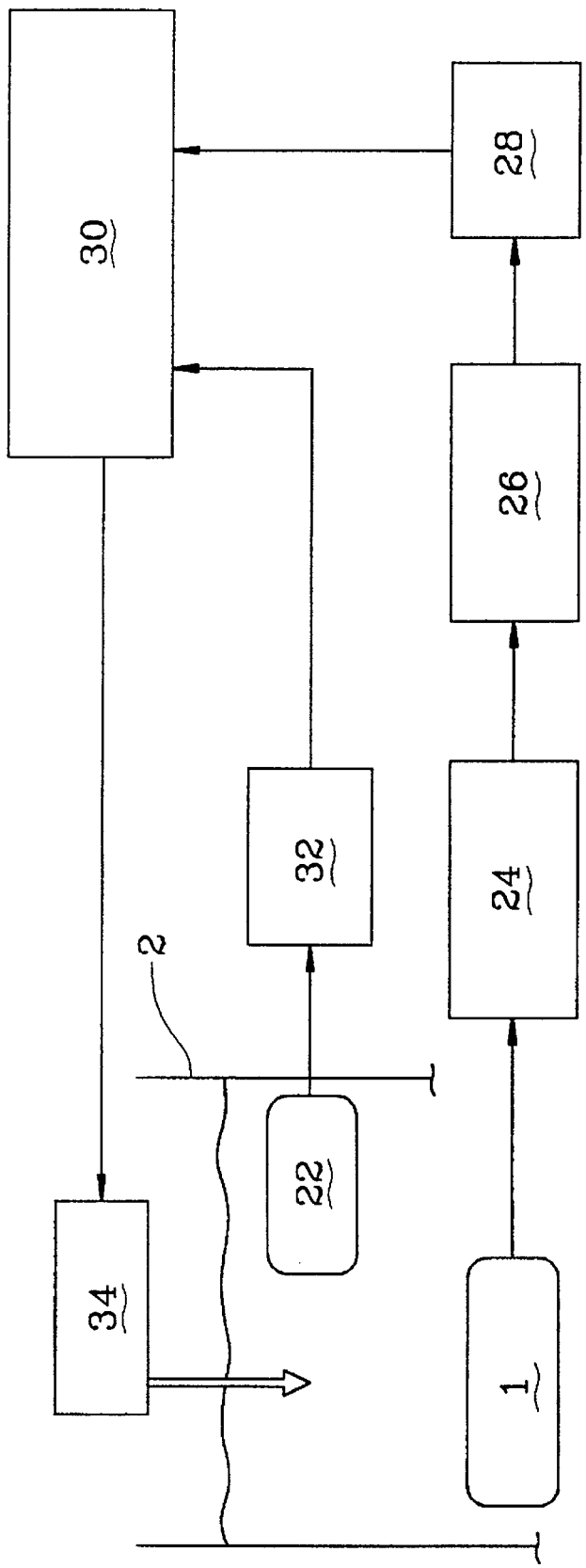
FIG. 3 illustrates the concentration control system of this invention.

A liquid toner concentration control system is shown in FIG. 3. A transverse flow viscometer 1 of FIG. 2 and a fluid temperature sensor 22 are located in the liquid toner chamber 2. If chamber 2 is part of the customer replaceable development cartridge, the sensor electronics would not be part of the chamber 2.

As the top plate 5 (FIG. 2) in viscometer 1 is continuously lifted and dropped, an electronic capacitance-to-frequency converter 24 converts the plate gap capacitance to a frequency. A low cost, frequency-to-voltage converter 26, such as the National LM2907, provides a voltage output proportional to the plate gap. A detector 28 consists of comparator circuits which detect the plate gap represented by two predetermined voltages, measures the time period between the first gap and the second gap, and provides a signal, preferably a pulse width proportional to the time period, defining that time period to a microprocessor 30. That time period is directly proportional to the liquid toner viscosity. To eliminate errors due to power supply variation, the detector 28 and the frequency to voltage converter 26 use the same voltage references.

A thermistor is located in the liquid toner tank 2 to provide, through analog/digital converter 32, the microprocessor 30 with the temperature of the fluid. The microprocessor uses an empirically derived look up table or algorithm to convert the temperature data and viscosity data to liquid toner concentration. If the concentration is low, microprocessor 30 causes the introduction of a fixed amount of toner concentrate through a liquid toner concentrate addition pump (not shown). The toner concentrate consists of a high (20 to 25 percent) solids toner mixture. In the preferred embodiment, the control system adds one gram of toner concentrate to raise the toner concentration in the sump approximately 0.1 percent solids. If the liquid toner concentration is high, the system adds a fixed amount of carrier fluid oil to the chamber 2. After each addition, microprocessor 30 will ignore the sensor data for an appropriate mixing time.

The following features and advantages are achieved by this invention:

Improved Percent Solids Measurement Range: This viscosity technique allows the system to measure and control the liquid toner concentration at eight percent solids. Traditional optical techniques are limited to a few percent solids.

Improved Signal to Noise Ratio: For the preferred embodiment the viscosity signal will change approximately ten percent per percent solids, but conductivity, density, and permittivity techniques are limited to less than one percent change in signal per percent solid.

Low Cost: The simple transverse flow viscometer uses gravity and a existing agitator mechanism to reduce cost. Since the initial plate gap and plate size are non critical, the parts are easily made and controlled.

Simple Electrical Interface: The simplicity of the design allows the temperature sensor and transverse flow viscometer in a customer replaceable development cartridge with only four electrical contacts, two for the thermistor and two for the viscometer. The electronics can be located in the machine and shared between all development cartridges, further reducing costs.

No Calibration of Development Cartridge: The transverse flow viscometer located in the fluid chamber requires no calibration. The integrator in the frequency to voltage converter will only require a one time calibration in the machine. The changes in the liquid toner permittivity due to percent solids will be compensated in the algorithm or look up table of the imaging device.

Small Measurement Error: Since the sensor uses gravity as the driving force and electronic techniques to eliminate power supply variations the measurement error is small. The worst case error is less than ±10 percent. In a preferred embodiment, the operating point is 8 percent solids and the estimated worst case measurement error is ±0.8 percent solids.

Fresh Fluid Measurement: The check valve feature continuously provides new fluid into the sensor.

Reduced Toner Plating and Contamination: The dual power supply oscillator technique reduces unwanted toner plating in the sensor.

What is claimed is:

1. Imaging apparatus comprising a chamber to contain liquid toner for imaging and a measuring device to measure the concentration of solids in a liquid in said chamber, said measuring device comprising a horizontal bottom plate in said chamber, a horizontal top plate moveable vertically with respect to said bottom plate in said chamber, means to measure the capacitance between said bottom plate and said top plate, means to measure the time period while said top plate falls in said liquid between a first predetermined capacitance measured by said means to measure and a second predetermined capacitance measured by said means to measure, and means to interpret said time difference as the concentration of said solids in said liquid for replenishing said toner.

2. The imaging apparatus as in claim 1 in which said bottom plate has a check valve through which said liquid is supplied between said bottom plate and said top plate by said vertical movement of said top plate.

3. A measuring device to measure the concentration of solids in a liquid comprising a horizontal bottom plate in a chamber for said liquid, a horizontal top plate moveable vertically with respect to said bottom plate in said chamber, means to measure the capacitance between said bottom plate and said top plate, means to measure the time period while said top plate falls in said liquid between a first predetermined capacitance measured by said means to measure and a second predetermined capacitance measured by said means to measure, and means to interpret said time difference as the concentration of said solids in said liquid.

4. The measuring device as in claim 1 in which said bottom plate has a check valve through which said liquid is supplied between said bottom plate and said top plate by said vertical movement of said top plate.

* * * * *